United States Patent
Gazzaley

(10) Patent No.: US 10,863,940 B2
(45) Date of Patent: Dec. 15, 2020

(54) METHODS OF ENHANCING PERFORMANCE ON A COGNITIVE TASK BY IMPROVED SELF-REGULATION OF INTERNAL DISTRACTION AND COMPUTER READABLE MEDIUM AND DEVICES FOR PRACTICING THE SAME

(71) Applicant: The Regents of the University of California, Oakland, CA (US)

(72) Inventor: Adam Gazzaley, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 506 days.

(21) Appl. No.: 15/507,922

(22) PCT Filed: Sep. 15, 2015

(86) PCT No.: PCT/US2015/050258
§ 371 (c)(1),
(2) Date: Mar. 1, 2017

(87) PCT Pub. No.: WO2016/044317
PCT Pub. Date: Mar. 24, 2016

(65) Prior Publication Data
US 2017/0249855 A1    Aug. 31, 2017

Related U.S. Application Data

(60) Provisional application No. 62/051,631, filed on Sep. 17, 2014.

(51) Int. Cl.
*G09B 5/06*    (2006.01)
*G09B 19/00*    (2006.01)
(Continued)

(52) U.S. Cl.
CPC ............ *A61B 5/168* (2013.01); *A61B 5/0482* (2013.01); *A61B 5/04842* (2013.01);
(Continued)

(58) Field of Classification Search
None
See application file for complete search history.

(56) References Cited

U.S. PATENT DOCUMENTS

2003/0013981 A1    1/2003  Gevins et al.
2006/0210955 A1    9/2006  Skoglund et al.

FOREIGN PATENT DOCUMENTS

WO    2000009007    2/2000
WO    2009049404    4/2009

OTHER PUBLICATIONS

Hasenkamp, et al., (2012) "Mind wandering and attention during focused meditation: A fine-grained temporal analysis of fluctuating cognitive states", NeuroImage, 59:750-760.
(Continued)

*Primary Examiner* — James B Hull
(74) *Attorney, Agent, or Firm* — Brian E. Davy; Bozicevic, Field & Francis LLP

(57) ABSTRACT

Provided are methods of enhancing the performance of a subject on a cognitive task by improved self-regulation of internal distraction. The methods include presenting a computer-based cognitive training program to a subject, where performance of the subject on the cognitive task is enhanced by the cognitive training program. Computer readable media and devices useful for practicing the methods of the present disclosure are also provided.

20 Claims, 8 Drawing Sheets

(51) Int. Cl.
*G09B 7/02* (2006.01)
*A61B 5/16* (2006.01)
*A61B 5/00* (2006.01)
*A61B 5/0482* (2006.01)
*A61B 5/0484* (2006.01)

(52) U.S. Cl.
CPC .......... *A61B 5/04845* (2013.01); *A61B 5/486* (2013.01); *A61B 5/6803* (2013.01); *G09B 5/06* (2013.01); *G09B 7/02* (2013.01); *G09B 19/00* (2013.01)

(56) References Cited

OTHER PUBLICATIONS

Lutz, et al., (2008) "Attention regulation and monitoring in meditation", Trends in Cognitive Neuroscience, 12(4):163-169.

Manna, et al., (2010) "Neural correlates of focused attention and cognitive monitoring in meditation", Brain Research Bulletin, 82:46-56.

Travis & Shear, (2010) "Focused attention, open monitoring and automatic self-transcending: Categories to organize meditations from Vedic, Buddhist and Chinese traditions", Consciousness and Cognition, 19(4):1110-1118.

Ziegler, et al., (Mar. 15, 2013) "Meditation-inspired cognitive training promotes self-regulation of internal distractions", UCSF Department of Neurology; Entertainment Software & Cognitive Neurotherapeutics Society (ESCoNS) Meeting Poster.

Ziegler et al. (2019) "Closed-loop digital meditation improves sustained attention in young adults" Nature Human Behavior, 3(7):746-757.

Mishra et al. (2020) "Closed-loop digital meditation for neurocognitive and behavioral development in adolescents with childhood neglect" Translational Psychiatry, 10:153, 13pgs.

FIG. 2
A
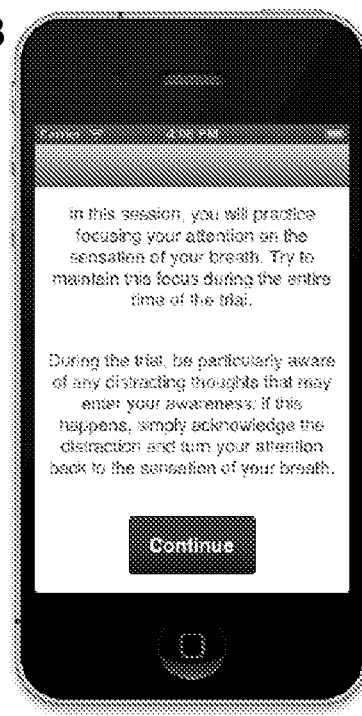
B
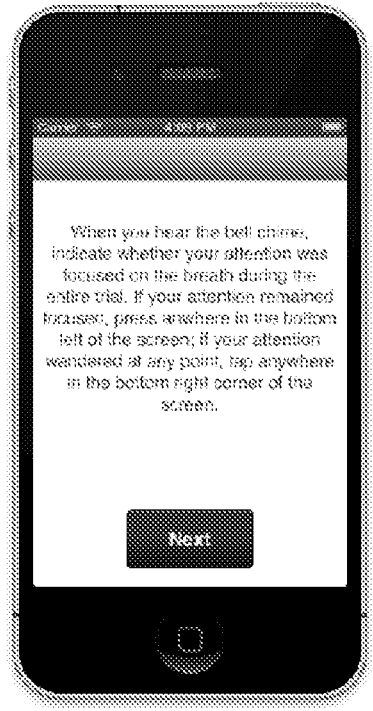
C
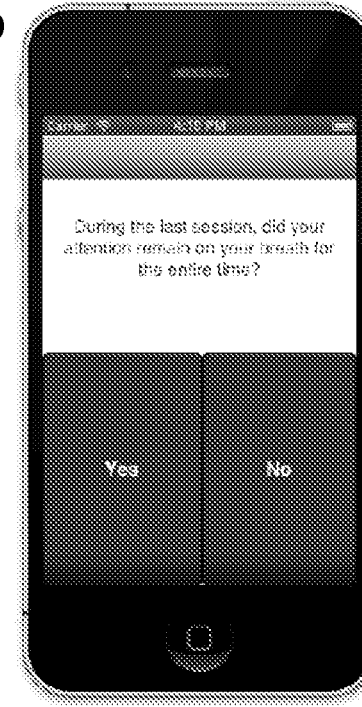
D

FIG. 2 (Cont'd)
E  F 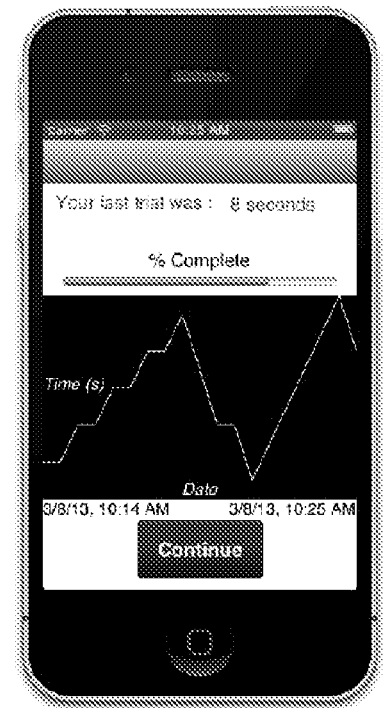

FIG. 4
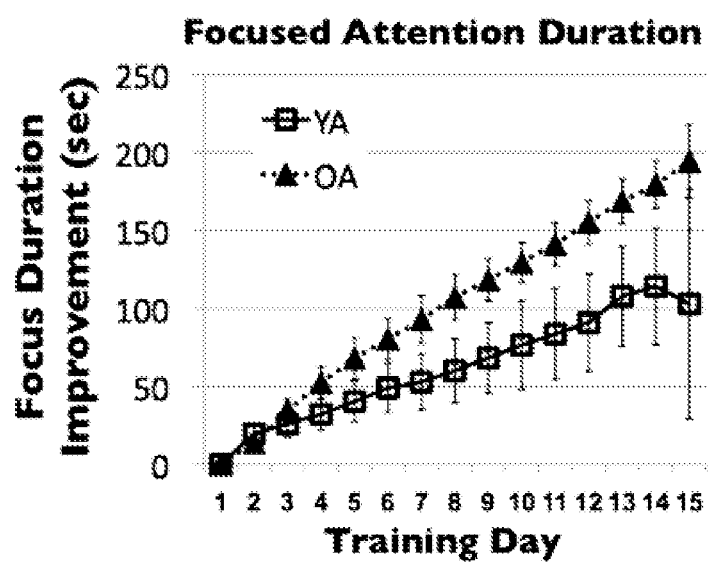
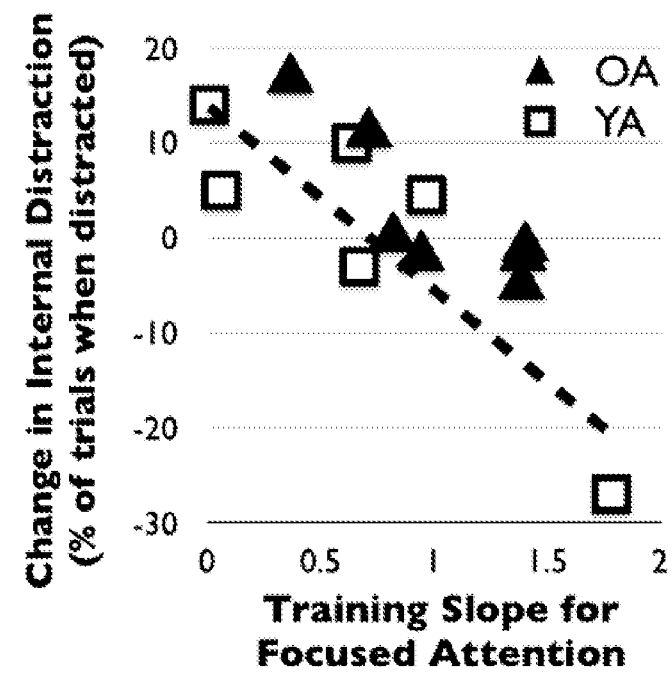

METHODS OF ENHANCING PERFORMANCE ON A COGNITIVE TASK BY IMPROVED SELF-REGULATION OF INTERNAL DISTRACTION AND COMPUTER READABLE MEDIUM AND DEVICES FOR PRACTICING THE SAME

CROSS REFERENCE TO RELATED APPLICATIONS

This application claims the benefit of U.S. Provisional Application No. 62/051,631, filed Sep. 17, 2014, which application is incorporated herein by reference in its entirety.

STATEMENT REGARDING FEDERALLY SPONSORED RESEARCH

This invention was made with government support under grant no. R21AG041071 awarded by the National Institutes of Health. The government has certain rights in the invention.

INTRODUCTION

An obstacle to achieving high-level performance on a wide variety of activities is interference by both external and internal distraction. Goal-directed activities themselves can either be oriented towards the external environment (e.g., visual and auditory attention and memory encoding), or involve an internal orientation (e.g., planning for the future, remembering past events, and maintaining items in short-term memory). During any of these activities, interference can arise from the external world in the guise of distracting sounds, images, smells, etc.; or internally in the form of distracting, unwanted, intrusive thoughts (e.g., mind-wandering). Self-regulation involves mechanisms of suppressing these distractions in order to maintain high-level performance on goal-directed tasks.

SUMMARY

Provided are methods of enhancing the performance of a subject on a cognitive task by improved self-regulation of internal distraction. The methods include presenting a computer-based cognitive training program to a subject, where performance of the subject on the cognitive task is enhanced by the cognitive training program. Computer readable media and devices useful for practicing the methods of the present disclosure are also provided.

Aspects of the present disclosure include methods of enhancing the performance of a subject on a cognitive task. The methods include presenting a computer-based cognitive training program to a subject. The cognitive training program includes presenting a subject with a first computer-based focused attention task at a difficulty level; determining a duration that the subject maintained focused attention during presentation of the first focused attention task; and presenting the subject with a second computer-based focused attention task at a difficulty level. The difficulty level of the second focused attention task is less than or the same as the difficulty level of the first focused attention task if the subject maintained focused attention for a duration less than a cutoff duration during presentation of the first focused attention task. The difficulty level of the second focused attention task is greater than the difficulty level of the first focused attention task if the subject maintained focused attention for a duration greater than a cutoff duration during presentation of the first focused attention task. The cutoff duration may be less than the entire duration of presentation of the first focused attention task. In other aspects, the cutoff duration is the entire duration of presentation of the first focused attention task. That is, the cutoff duration and the duration for which the focused attention task is presented may be the same. According to the methods, the performance of the subject on the cognitive task is enhanced by the cognitive training program.

In certain aspects, the first focused attention task and the second focused attention task are independently selected from an internally-directed focused attention task, and an externally-directed focused attention task. According to certain embodiments, the first and/or second focused attention task is an internally-directed focused attention task selected from: the subject directing attention to the subject's breath sensations, the subject directing attention to a mental image, the subject directing attention to a phrase held in the subject's mind, and the subject directing attention to a phrase held in an internal body part of the subject other than the mind. In certain aspects, the first and/or second focused attention task is an externally-directed focused attention task selected from: the subject directing attention to a visual stimulus, and the subject directing attention to an auditory stimulus. The first focused attention task and the second focused attention task may be the same, e.g., the same type of task). Alternatively, the first focused attention task and the second focused attention task may be the different, e.g., the two tasks are different types of tasks.

The difficulty level of the first focused attention task and second focused attention task may be independently determined using any suitable approaches, including combinations of approaches. In certain aspects, the difficulty level of the first focused attention task, the second focused attention task, or both, is determined by the duration for which the focused attention task is presented. Alternatively, or additionally, the difficulty level of the first focused attention task, the second focused attention task, or both, may be determined by a context in which the focused attention task is presented. A context for modulating the difficulty level of a focused attention task includes, e.g., presenting one or more stimuli to the subject. Stimuli of interest include, e.g., auditory and/or visual stimuli. According to aspects in which a visual stimulus is presented to the subject during presentation of the focused attention task, the visual stimulus may be presented to the subject on a display, e.g., a display of a smartphone, tablet computer, head-up display (HUD) device, smartwatch, laptop computer, desktop computer, any other convenient display, and combinations thereof. Presenting an auditory stimulus to the subject may include producing a sound such as white noise, a tone, a song, and/or a conversation.

In certain aspects, determining the duration that the subject maintained focused attention during presentation of the first focused attention task includes receiving an indication from the subject of the duration for which the subject maintained focused attention during presentation of the first focused attention task. The indication may require a response from the subject, e.g., a response to an interrogatory in which the subject is asked to indicate the duration for which the subject maintained focused attention during presentation of the first focused attention task. In certain aspects, the subject responds via an input device, such as a touch-screen display, a mouse, a keyboard, a microphone, or the like.

According to certain embodiments, receiving an indication from the subject of the duration for which the subject maintained focused attention during presentation of the first focused attention task includes measuring one or more biological parameters of the subject. In certain aspects, the biological parameter includes neurological activity of the subject. Neurological activity may be measured using any convenient approach, and in certain embodiments includes measuring neurological activity by electroencephalography (EEG). When the neurological activity is measured by EEG, the measurements/recordings are optionally obtained using an EEG headset worn by the subject. Other biological parameters may be used as an indication from the subject of the duration for which the subject maintained focused attention during presentation of the first focused attention task. In some embodiments, the one or more biological parameters includes eye movement of the subject.

In certain aspects, prior to presenting the first focused attention task, the second focused attention task, or both, the method includes instructing the subject to notice internal distraction during presentation of the first focused attention task, the second focused attention task, or both. According to certain embodiments, after presenting the first focused attention task, the second focused attention task, or both, the method includes reporting to the subject the duration for which the subject was able to maintain focused attention during presentation of the first focused attention task, the second focused attention task, or both.

The computer-based cognitive training program may be presented to the subject using any device of interest. In certain aspects, the training program is presented on a computer device selected from: a smartphone, a tablet computer, a head-up display (HUD) device, a smartwatch, a laptop computer, a desktop computer, and combinations thereof.

The cognitive task that is enhanced by presentation of the computer-based cognitive training program may vary, and in certain instances is a visual search task. Subjects of interest include younger adults, older adults, and the like. According to certain embodiments, the subject is an older adult. The subject may be a healthy subject, or the subject may have a mental disease including, but not limited to, Attention Deficit Hyperactivity Disorder (ADHD, both distractibility and hyperactive behaviors), Post-Traumatic Stress Disorder (PTSD, intrusive recollections triggered by external cues), Major Depressive Disorder (ruminations, impairments in cognition and attention), Obsessive Compulsive Disorder (OCD, uncontrollable anxieties/obsessions, compulsive behaviors), traumatic brain injury (TBI), Substance Dependence Disorders (uncontrollable cravings, contextual triggers for relapse), or the like.

Also provided are non-transitory computer-readable media that include instructions stored thereon for causing a computer device to implement the methods of the present disclosure, e.g., any methods according to the embodiments (including any combinations thereof) described elsewhere herein. Computer devices that include such non-transitory computer-readable media are also provided.

BRIEF DESCRIPTION OF THE FIGURES

FIG. 2 shows certain aspects of presenting a cognitive training program to a subject according to one embodiment of the present disclosure.

DETAILED DESCRIPTION

Figure 1:
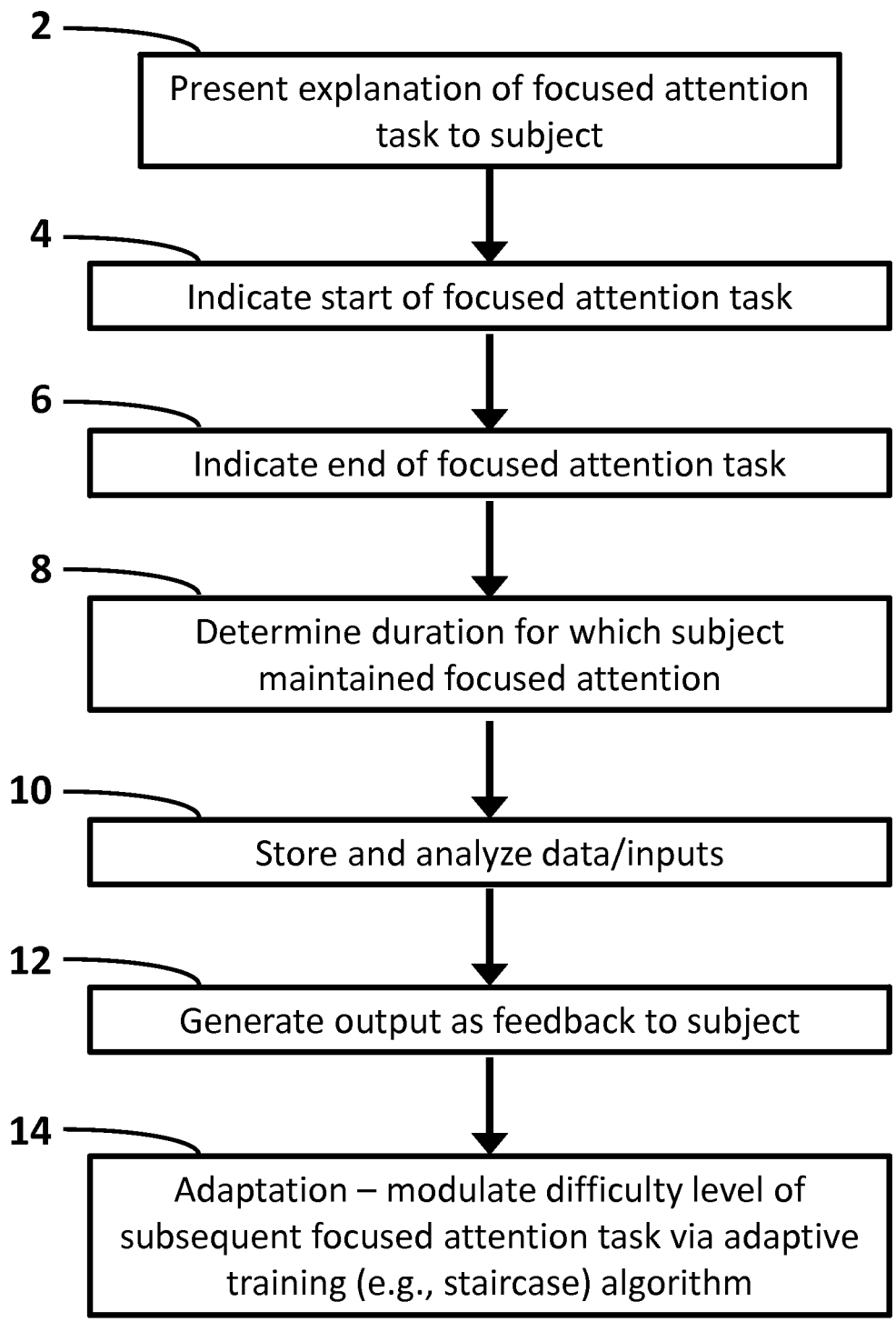
FIG. 1 is a flow diagram illustrating steps of a method according to one embodiment of the present disclosure.

Provided are methods of enhancing the performance of a subject on a cognitive task. The methods include presenting a computer-based cognitive training program to a subject, where performance of the subject on the cognitive task is enhanced by the cognitive training program. Computer readable media and devices useful for practicing the methods of the present disclosure are also provided.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within by the methods. The upper and lower limits of these smaller ranges may independently be included in the smaller ranges and are also encompassed within by the methods, subject to any specifically excluded limit in the stated range. Where the stated range includes one or both of the limits, ranges excluding either or both of those included limits are also included in the methods.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods, computer readable media and devices are now described.

Any publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or devices. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

As summarized above, the present disclosure provides methods of enhancing the performance of a subject on a cognitive task.

The methods include presenting a computer-based cognitive training program to a subject. By "computer-based" is meant that the training program is presented to the subject using a computer, e.g., a computer device such as a smartphone, a tablet computer, a head-up display (HUD) device, a smartwatch, a laptop computer, a desktop computer, or any combination thereof (e.g., certain portions of the training program may be presented to the subject using one type of computer device, while other portions may be presented to the subject using one or more other types of computing devices).

The cognitive training program includes presenting a subject with a first computer-based focused attention task. According to certain aspects, the subject is a human subject, e.g., a female or male human subject. Human subjects of interest include children and adults. In certain aspects, the human subject is from 4 years old to 100 years old, such as from 8 years old to 100 years old, from 9 years old up to 90 years old, from 10 years old up to 80 years old, from 11 years old up to 75 years old, or from 12 years old up to 70 years old. According to certain embodiments, the human subject is a child (newborn up to 18 years old). Children of interest include infants (newborn up to 1 year old), toddlers (1 year old up to 3 years old), preschoolers (3 years old up to 4 years old), children in middle childhood (4 years old up to 11 years old, such as 6 years old up to 8 years old, or 8 years old up to 11 years old), young teens (11 years old up to 14 years old) and teenagers (14 years old up to 18 years old). When the subject is a human adult, the subject may be a younger adult (an 18-30 year old adult, e.g., a 21-28 year-old adult)), a middle-age adult (a 31-49 year-old adult), or an older adult (a 50 year-old or older adult (e.g., a 57-75 year-old adult)).

In certain aspects, the subject is a healthy subject, e.g., free of a mental disease. In other aspects, the subject has a mental disease, such as Attention Deficit Hyperactivity Disorder (ADHD, both distractibility and hyperactive behaviors), Post-Traumatic Stress Disorder (PTSD, intrusive recollections triggered by external cues), Major Depressive Disorder (ruminations, impairments in cognition and attention), Obsessive Compulsive Disorder (OCD, uncontrollable anxieties/obsessions, compulsive behaviors), traumatic brain injury (TBI), Substance Dependence Disorders (uncontrollable cravings, contextual triggers for relapse), or the like.

In certain aspects, the present disclosure provides methods of diagnosing such disorders, e.g., by presenting one or more focused attention tasks to a subject (e.g., a subject suspected of having any of the above disorders), quantifying the subject's ability to maintain focused attention during the focused attention task(s), and diagnosing the subject as having any of the above disorders if the subject's ability to maintain focused attention is below a cutoff ability, e.g., as determined by the duration for which the subject is able to maintain focused attention during the focused attention task at a particular (e.g., standardized) difficulty level.

Similarly, as the methods of the present disclosure improve a subject's ability to maintain focused attention (e.g., by improved regulation of internal distraction/mind wandering), the present disclosure provides methods of treating a subject having a mental disease in which an underlying etiology or symptom of the disease is poor regulation of internal distraction/mind wandering (e.g., any of the mental diseases recited above). According to certain embodiments, the methods include presenting a computer-based cognitive training program according to any of the embodiments described elsewhere herein to a subject having the mental disease, where the training program enhances the subject's ability to regulate internal distraction, thereby treating the subject having the disease.

As used herein, a first or second "focused attention task" is a task in which the subject is instructed to direct sustained and selective attention to a single object to the exclusion of any other objects internal or external to the subject. The object to which the subject's focused attention is directed may vary. According to certain embodiments, the focused attention task includes the subject directing focused attention to an object traditionally associated with "focused meditation" or "focused attention meditation." Details regarding focused attention meditation may be found, e.g., in Hasenkamp et al. (2012) *NeuroImage* 59:750-760, Manna et al. (2010) *Brain Research Bulletin* 82:46-56, Lutz et al. (2008) *Trends in Cognitive Neuroscience* 12(4):163-169, and Travis & Shear (2010) *Consciousness and Cognition* 19(4):1110-1118.

In certain aspects, the first focused attention task and the second focused attention task are independently selected from an internally-directed focused attention task, and an externally-directed focused attention task. Internally-directed focused attention tasks of interest include, but are not limited to, the subject directing attention to an object selected from the subject's breath sensations (e.g., where the subject focuses attention on her/his breath during inhalation and exhalation), a mental image (e.g., a mental image of an object), a word or phrase (e.g., a mantra) held in the subject's mind or internal body part of the subject other than the mind), a goal, or the like.

Externally-directed focused attention tasks of interest include, but are not limited to, the subject directing attention to an object selected from a visual stimulus, and an auditory stimulus. Visual stimuli that may be presented to the subject as an object of focused attention include real objects, or object images (e.g., an object image presented to the subject via a display of a computer device (e.g., a smartphone, tablet, head-up display (HUD) device, smartwatch, or the like). Auditory stimuli that may be presented to the subject as an object of focused attention include, e.g., a tone.

The first focused attention task and the second focused attention task may be the same or different. By "same" is meant the object to which the subject's focused attention is directed during presentation of the first focused attention task is the same object to which the subject's focused attention is directed during presentation of the second focused attention task. By "different" is meant the object to which the subject's focused attention is directed during presentation of the first focused attention task is different from the object to which the subject's focused attention is directed during presentation of the second focused attention task.

According to certain embodiments, both the first focused attention task and the second focused attention task are internally-directed focused attention tasks, which internally-directed focused attention tasks may be the same or different. In other aspects, both the first focused attention task and the second focused attention task are externally-directed focused attention tasks, which externally-directed focused attention tasks may be the same or different. In certain embodiments, the first focused attention task is an internally-directed focused attention task and the second focused attention task is an externally-directed focused attention task. In other aspects, the first focused attention task is an externally-directed focused attention task and the second focused attention task is an internally-directed focused attention task.

The difficulty level of the focused attention task may be determined by one or more factors selected by a designer of the training program. For example, the difficulty level of the first focused attention task, the second focused attention task, or both, may be determined at least in part by the duration for which the focused attention task is presented. The duration may vary according to the subject's ability to maintain focused attention, and in certain aspects is from 1 second to 10 minutes (e.g., from 1 to 250 seconds). According to certain embodiments, the duration of presentation of a focused attention task is from 1 to 5 seconds, from 6 to 10 seconds, from 11 to 15 seconds, from 16 to 20 seconds, from 21 to 25 seconds, from 26 to 30 seconds, from 31 to 35 seconds, from 36 to 40 seconds, from 41 to 45 seconds, from 46 to 50 seconds, from 51 to 55 seconds, from 56 to 60 seconds, from 61 to 65 seconds, from 66 to 70 seconds, from 71 to 75 seconds, from 76 to 80 seconds, from 81 to 85 seconds, from 86 to 90 seconds, from 91 to 95 seconds, from 96 to 100 seconds, from 101 to 105 seconds, from 106 to 110 seconds, from 111 to 115 seconds, from 116 to 120 seconds, from 121 to 125 seconds, from 126 to 130 seconds, from 131 to 135 seconds, from 136 to 140 seconds, from 141 to 145 seconds, from 146 to 150 seconds, from 151 to 155 seconds, from 156 to 160 seconds, from 161 to 165 seconds, from 166 to 170 seconds, from 171 to 175 seconds, from 176 to 180 seconds, from 181 to 185 seconds, from 186 to 190 seconds, from 191 to 195 seconds, from 196 to 200 seconds, from 201 to 205 seconds, from 206 to 210 seconds, from 211 to 215 seconds, from 216 to 220 seconds, from 221 to 225 seconds, from 226 to 230 seconds, from 231 to 235 seconds, from 236 to 240 seconds, from 241 to 245 seconds, from 246 to 250 seconds, etc.

In certain aspects, the difficulty level of the first focused attention task, the second focused attention task, or both, is determined at least in part by a context in which the focused attention task is presented. By "context" is meant an environment in which the subject performs the focused attention task, and may include presenting one or more stimuli (e.g., one or more potentially distracting stimuli) to the subject during presentation of the focused attention task. Stimuli of interest include, but are not limited to, visual and/or auditory stimuli. For example, in certain aspects, the difficulty level is modulated by presenting a visual stimulus to the subject while the subject is performing the focused attention task (e.g., an internally- or externally-directed focused attention task). Presenting a visual stimulus to the subject may include requiring the subject to perform an internally- or externally-directed focused attention task with his/her eyes open, and displaying a real object in the subject's field of view. Similarly, an image of an object may be displayed in the subject's field of view (e.g., on a display of a smartphone, tablet computer, head-up display (HUD) device, smartwatch, laptop computer, desktop computer, or the like).

According to certain embodiments, the difficulty level is modulated by presenting an auditory stimulus to the subject while the subject is performing the focused attention task (e.g., an internally- or externally-directed focused attention task). Presenting an auditory stimulus to the subject may include producing a sound such as white noise, a tone, a song, and/or a conversation. In certain aspects, the sound is produced by the computer (e.g., via speaker(s) or headphones) being used to present the training program to the subject (e.g., a smartphone, tablet computer, head-up display (HUD) device, smartwatch, laptop computer, desktop computer, or the like), or a separate sound-producing device within audible range of the subject as the subject performs the focused attention task. The volume and/or type of auditory stimulus may be selected to bring about a desired level of difficulty. For example, a difficulty level achieved using louder and/or more complex auditory stimuli will generally be greater than a difficulty level achieved using quieter and/or less complex auditory stimuli. For example, presenting the sound of conversation (more complex) to the subject will typically effect a greater level of difficulty than presenting white noise (less complex) to the subject. In certain aspects, the difficulty level is determined using one or more visual stimuli and one or more auditory stimuli.

Based on the duration for which the subject maintained focused attention during presentation of the first focused attention task, the difficulty level of the second focused attention task may be decreased, remain the same, or increased relative to the difficulty level of the first focused attention task. In certain aspects, the methods include quantifying the subject's performance for maintaining focused attention during a focused attention task, providing feedback to the subject regarding the subject's performance, and adapting the difficulty level of a subsequently-presented focused attention task based on the quantification of the subject's performance on the preceding focused attention task.

The difficulty level of a subsequently-presented focused attention task may be adapted using a variety of approaches. According to certain embodiments, the adaptation is carried out by a psychometric analysis method such as a staircase algorithm/procedure and/or maximum likelihood procedure to adaptively determine the subject's ability to maintain focused attention and adapt the difficulty level of a subsequently-presented focused attention task accordingly.

As summarized above, the methods include determining a duration that the subject maintained focused attention during presentation of the first focused attention task. The duration for which the subject maintained focused attention may be determined using any suitable/convenient approach. According to certain embodiments, determining the duration that the subject maintained focused attention during presentation of the first focused attention task includes receiving an indication from the subject of the duration for which the subject maintained focused attention during presentation of the first focused attention task. For example, prior to presentation of the first focused attention task, the subject may be instructed to be aware of the presence of internal distraction (e.g., mind wandering) while the subject performs the first focused attention task. According to certain embodiments, determining a duration for which the subject maintained focused attention includes requiring the subject—after presentation of the first focused attention task—to indicate whether the subject maintained focused attention for the entire duration of the first focused attention task. That is, in certain aspects, determining the duration for which the subject maintained focused attention includes determining whether the subject maintained focused attention for the entire duration of the first focused attention task, and not the specific duration if the subject did not maintain focused attention during the entire duration of the task. This binary approach for determining the duration of the subject's focused attention is sufficient, e.g., when the cutoff duration for determining whether to increase (or decrease) the difficulty level of a subsequently-presented focused attention task is the same as the duration of the first focused attention task.

In certain aspects, if internal distraction resulted in a loss of focused attention during the presentation of the focused attention task, the method may include the subject indicating (e.g., via a touchscreen display of a smartphone, tablet, smartwatch, etc.) as the internal distraction occurs during presentation of the focused attention task, so that a specific duration of focused attention may be determined based on a response by the user.

As set forth above, according to certain embodiments, determining the duration for which the subject maintains focused attention requires a response from the subject. In certain aspects, the subject responds via an input device, such as a touch-screen display, a mouse, a keyboard, a microphone, or any other convenient input device.

Other strategies may be employed for determining the duration for which a subject maintains focused attention during presentation of the focused attention task. For example, determining the duration may include measuring one or more biological parameters of the subject. In certain aspects, the biological parameter includes neurological activity. Various approaches for measuring neurological activity as it relates to focused attention may be employed. According to certain embodiments, neurological activity of the subject as the subject performs the focused attention task is measured by electroencephalography (EEG), in which voltage fluctuations resulting from ionic current flows within the neurons of the brain may be recorded using one or more electrodes placed on the scalp of the subject. In certain aspects, EEG recording are obtained using an EEG headset worn by the subject during presentation of at least one focused attention task of the training program. EEG patterns correlating with focused attention have been reported, e.g., by Travis & Shear (2010) *Consciousness and Cognition* 19(4):1110-1118. In certain aspects, monitoring focused attention to determine the duration that the subject maintained focused attention includes recording an EEG frequency band selected from gamma (30-50 Hz), Beta2 (20-30 Hz), Beta1 (13-20 Hz), alpha (8-12 Hz), theta (4-8 Hz), delta (1-4 Hz), or any combination thereof (see, e.g., Mantini et al. Electrophysiological signatures of resting state networks in the human brain. Proc Natl Acad Sci USA (2007) vol. 104 (32) pp. 13170-5).

According to certain embodiments, neurological activity of the subject as the subject performs the focused attention task is measured by functional imaging, such as fMRI. In fMRI, brain activity by is measured by detecting associated changes in blood flow. Neural measures associated with mind-wandering and the suppression of internal distractors may be assessed using fMRI (both regional activity and network connectivity). fMRI neuro-imaging has elucidated neural correlates of these phenomena. During mind-wandering there is an increase in neural activity in the default network that is dependent on the nature of the ongoing activity (7; 12; 44) (a network of brain areas that are more active during non-task oriented behaviors (23; 44)), and the predilection of participants to mind-wander in general correlates with increased activity in this network during cognitive tasks (7; 9). Studies have demonstrated activity in frontal executive circuits during mind-wandering. Details regarding fMRI and how it may be applied to detect focused attention and mind wandering/internal distraction are found, e.g., in Christoff et al. (2009) *PNAS* 106(21):8719; Mason et al. (2007) *Science* 315(5810):393-395; Preminger et al. (2011) *NeuroImage* 54(2):1692-702; Buckner et al. (2008) *Annals of the New York Academy of Sciences* 1124(1):1-38; and Andrews-Hanna et al. (2010) *J. Neurophysiology Annals of the New York Academy of Sciences* 1124(1):1-38.

In certain aspects, the biological parameter utilized to determine the duration for which the subject maintains focused attention during presentation of the focused attention task is the subject's eye movements. The subject's eye movements may be tracked using any suitable eye movement tracking hardware/software. In certain aspects, a camera associated (or integrated) with the computer device that presents the focused attention task to the subject, along with suitable eye tracking software loaded on the computer device, may be used to detect eye movements of the subject associated with focused attention and internal distraction as a means for determining the duration for which the subject maintains focused attention during presentation of the focused attention task. Computer devices (e.g., mobile devices) capable of tracking a user's eye movements are known and described, e.g., in US Patent Application Publication Nos. US 2014/0145935 and US 2014/0009739, the disclosures of which are incorporated herein by reference in their entireties for all purposes.

Steps of a method according to one embodiment of the present disclosure are illustrated in FIG. 1. In this example, the method includes the step of presenting an explanation of a first focused attention task (step 2); indicating that the focused attention task has started (step 4); indicating that the focused attention task has ended (step 6); determining the duration for which the subject maintained focused attention (step 8); storing and analyzing data (e.g., the duration that the subject maintained focused attention, and the like) and any inputs provided by the subject (e.g., one or more indications by the subject of loss of focused attention (e.g., an occurrence of internal distraction/mind wandering)) (step 10); generating output as feedback to the subject (e.g., informing the subject of his/her performance level on the task) (step 12); and an adaptation step (step 14) whereby the difficulty level of a subsequent (second) focused attention task presented as part of the training program may be modulated using an adaptive training algorithm (e.g., a staircase algorithm) based on the subject's ability to maintain focused attention during presentation of the first focused attention task.

An example of how a focused attention task may be presented to a subject according to one embodiment of the present disclosure is shown in FIG. 2. In this example, the focused attention task is presented to the subject via a smartphone. As shown in Panel A, the presentation may begin by welcoming the subject and instructing the subject to ensure that she/he is in a suitable environment for performing the focused attention task. As shown in Panel B, a subsequent screen presented to the subject may provide a description of the focused attention task and instructions on how to proceed if internal distraction/mind wandering occurs. As shown in Panel C, a subsequent screen may be the final screen prior to the commencement of the focused attention task, instructing the subject to indicate—upon completion of the task as indicated by a signal from the computer device (e.g., a chime)—whether focused attention was maintained for the entire duration of the focused attention task. Once the computer signals that the focused attention task has terminated, a screen may appear requiring the subject to indicate whether the subject maintained focused attention for the entire duration of the task (see Panel D). Subsequent screens according to this embodiment provide the subject with information regarding the duration of a prior focused attention task, and include feedback to the subject, e.g., which may include a visual (e.g., a graph) or textual indication of any training-related improvements realized by the subject.

It will be appreciated that the training program presented to the subject may include presenting more than a first and second focused attention task. According to certain aspects, the training program includes presenting 2, 3, 4, 5, 10, 15, 20, 25, 30, 35, 40, 45, 50, 55, 60, 65, 70, 75, 80, 85, 90, 95, 100 or more focused attention tasks, the difficulty levels of which may, in certain aspects, be adapted based on the duration for which the subject was able to maintain focused attention during presentation of a preceding focused attention task at a selected difficulty level. The training program may include presenting one or more focused attention tasks to a subject each day over a number of days (e.g., a number of consecutive or non-consecutive days), such that the training program includes multiple "sessions" where the one or more presentations of a focused attention task during a day constitutes a single session. The training program may be presented for any number of days, e.g., until a desired level of ability to maintain focused attention and/or enhanced performance on the cognitive task is achieved. In certain aspects, the entire training program is presented on a single day. In other aspects, the entire training program lasts from 2 to 7 days, from 8 to 14 days, from 15 to 21 days, from 22 to 28 days, or any other number of days suitable for achieving a desired result.

The cognitive task for which performance of the subject is enhanced using the method of the present disclosure may vary. The surprising findings presented in the Experimental section below that a cognitive training program that includes focused attention training enhanced the performance of an untrained cognitive task (a visual search task) indicates that the methods of the present disclosure are applicable for enhancing performance on a wide variety of cognitive tasks, and enhances cognitive abilities generally.

Computer Readable Media and Devices

Aspects of the present disclosure further include computer readable media and devices. In certain aspects, provided are non-transitory computer readable media comprising instructions stored thereon for causing a computer device to implement the methods of the present disclosure, including any embodiments of the methods described elsewhere herein. For example, the computer readable medium may include instructions to cause the computer device to present a computer-based cognitive training program to a subject, where presenting the cognitive training program includes: presenting a subject with a first focused attention task at a difficulty level; determining a duration that the subject maintained focused attention during presentation of the first focused attention task; and presenting the subject with a second computer-based focused attention task at a difficulty level, where the difficulty level of the second focused attention task is less than or the same as the difficulty level of the first focused attention task if the subject maintained focused attention for a duration less than a cutoff duration during presentation of the first focused attention task, and where the difficulty level of the second focused attention task is greater than the difficulty level of the first focused attention task if the subject maintained focused attention for a duration greater than a cutoff duration during presentation of the first focused attention task.

Physical computer readable media of the present disclosure include, but are not limited to, disks (e.g., magnetic or optical disks), solid-state storage drives, cards, tapes, drums, punched cards, barcodes, and magnetic ink characters and other physical medium that may be used for storing representations, instructions, and/or the like.

Also provided are computer devices that carry out the methods of the present disclosure. In certain aspects, the computer device includes a non-transitory computer readable medium according to any of the embodiments described above. According to certain embodiments, the computer device does not include instructions for carrying out the methods of the present disclosure, but rather serves as a portal for presenting a cognitive training program the instructions for which are stored on a remote server.

In certain aspects, the computer device is selected from a smartphone, a tablet computer, a head-up display (HUD) device, a smartwatch, a laptop computer, and a desktop computer. Smartphones or personal digital assistant (PDA) devices of interest include, but are not limited to, the Apple iPhone, Android operating system-based smartphones commercially available from any number of manufacturers (e.g., Samsung, HTC, Huawei, Alcatel, Acer, Sony Ericsson, LG, Google Nexus, ZTE, Motorola, etc.), Windows-based smartphones, and the like. Smartwatches of interest include the Apple Watch, Android-based smartwatches (e.g., smartwatches running the Android Wear operating system), and the like. Tablet computers of interest include, but are not limited to, the Apple iPad, Android operating system-based tablets commercially available from any number of manufacturers (e.g., Samsung, Motorola, Acer, Archos, Dell, Sony, Toshiba, ZTE, etc.), Windows-based tablet computers, and the like. According to certain embodiments, the computer is a head-up display (HUD) device. Any suitable HUD device may be employed. In certain aspects, the HUD device is selected from a HUD device sold by Oculus VR® (e.g., an Oculus Rift HUD device), a HUD device sold by Sony Computer Entertainment (e.g., a Project Morpheus HUD device), a HUD device sold by Samsung Electronics Co.

Ltd. (e.g., a Gear VR HUD device), a HUD device sold by Google (e.g., Google Glass), or any other HUD device suitable for presenting a cognitive training program according to the methods of the present disclosure.

Figure 3:
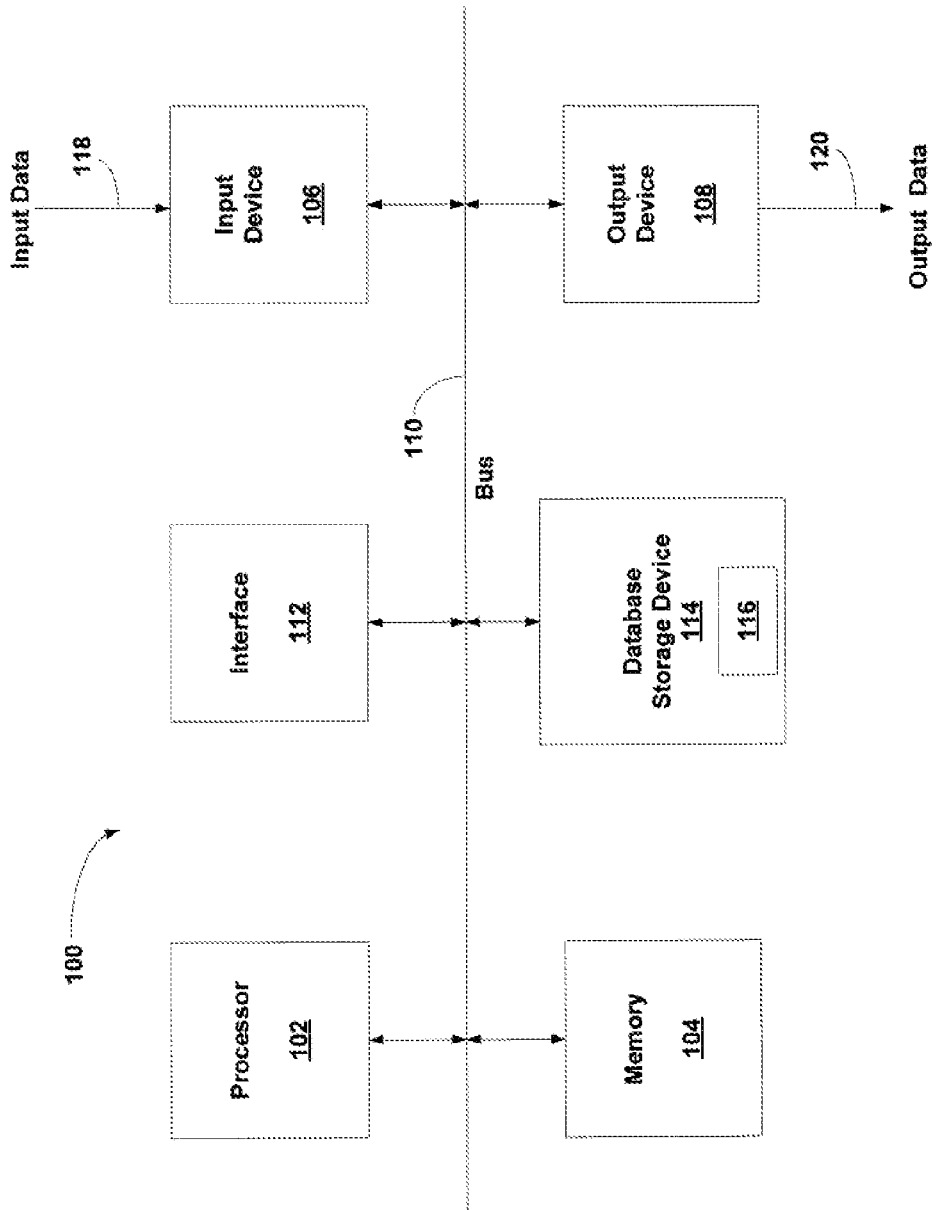
FIG. 3 schematically illustrates an example device useful for practicing the methods of the present disclosure.

The components and configuration thereof of the computer may vary. A computer device having a configuration according to a generalized embodiment of the present disclosure is schematically illustrated in FIG. 3. Processor 100 generally comprises at least one processor 102, or processing unit or plurality of processors, memory 104, at least one input device 106 and at least one output device 108, coupled together via a bus or group of buses 110. In certain embodiments, input device 106 and output device 108 could be the same device. An interface 112 can also be provided for coupling the processing system 100 to one or more peripheral devices, for example interface 112 could be a PCI card or PC card. At least one storage device 114 which houses at least one database 116 can also be provided. The memory 104 can be any form of memory device, for example, volatile or non-volatile memory, solid state storage devices, magnetic devices, etc. In certain aspects, the memory is a non-volatile computer readable medium as described above having instructions stored thereon for causing the computer to implement the methods of the present disclosure. Processor 102 may comprise more than one distinct processing device, for example to handle different functions within the processing system 100. Input device 106 receives input data 118 and can comprise, for example, a touchscreen display, a trackpad, a keyboard, a pointer device such as a pen-like device (e.g., a stylus) or a mouse, audio receiving device for voice controlled activation such as a microphone, data receiver or antenna such as a modem or wireless data adaptor, data acquisition card, etc. Input data 118 could come from different sources, for example keyboard instructions in conjunction with data received via a network. Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 could be distinct and derived from different output devices, for example a visual display on a monitor in conjunction with data transmitted to a network. A subject could view data output, or an interpretation of the data output, on, for example, a display/monitor or using a printer. Storage device 114 can be any form of data or information storage means, for example, volatile or non-volatile memory, solid state storage devices, magnetic devices, etc.

In use, processing system 100 is adapted to allow data or information to be stored in and/or retrieved from, via wired or wireless communication means, at least one database 116. Interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. Processing system 100 may be any form of terminal, server, specialized hardware, or the like.

Processing system 100 may be a part of a networked communications system. Processing system 100 could connect to a network, for example the Internet or a WAN. Input data 118 and output data 120 could be communicated to other devices via the network. The transfer of information and/or data over the network can be achieved using wired communications means or wireless communications means. A server can facilitate the transfer of data between the network and one or more databases. A server and one or more databases provide an example of an information source.

Accordingly, the processing computing system environment 100 illustrated in FIG. 3 may operate in a networked environment using logical connections to one or more remote computers. The remote computer may be a personal computer, a server, a router, a network PC, a peer device, or other common network node, and typically includes many or all of the elements described above.

The logical connections depicted in FIG. 1A include a local area network (LAN) and a wide area network (WAN), but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 3 are exemplary and other means of establishing a communications link between multiple computers may be used.

FIG. 3 is intended to provide a brief, general description of an illustrative and/or suitable exemplary environment in which embodiments of the methods of the present disclosure may be implemented. FIG. 3 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

Utility

The methods of the present disclosure find use a variety of contexts, and in certain instances, improve the subject's ability to regulate internal distraction (e.g., mind wandering). Failure to adequately control and regulate the impact of internal distraction can lead to significant impairment in cognition (e.g., performance on cognitive tasks unrelated to the focused attention tasks presented as part of the cognitive training program), social conduct, and emotional regulation. Pathological failure to regulate internal distraction is believed to play an important role in a range of mental illnesses, including ADHD (both distractibility and hyperactive behaviors), PTSD (intrusive recollections triggered by external cues), Major Depressive Disorder (ruminations, impairments in cognition and attention), Obsessive Compulsive Disorder (uncontrollable anxieties/obsessions, compulsive behaviors), and Substance Dependence Disorders (uncontrollable cravings, contextual triggers for relapse). Accordingly, in addition to enhancing cognitive performance, the methods of the present disclosure find use in diagnosing and treating subjects having mental illnesses in which internal distraction plays a role.

In certain aspects, software applications can be created and distributed on different platforms (smartphones, tablets, head-up display (HUD) devices, smartwatches via the internet, etc.) to be used by individuals to help them and/or healthcare professionals both understand their internal distractibility and better control internal distraction, resulting in improvement of clinical symptoms, cognition, stress and sleep. Moreover, the methods of the present disclosure find use for individuals that experience difficulty engaging in meditation practices to learn how to control their internal distraction.

Approaches for improving self-regulation include in-person training sessions and self-guided training sessions. In-person training sessions lack the convenience required for widespread adoption and completion of the training program, while self-guided training fails to provide the trainee with feedback and performance-based adaptation of difficulty levels for tracking progress and maximizing the effectiveness of the training. The methods of the present disclosure make up the deficiencies of in-person approaches, as the training may be performed on a mobile device at a time and location convenient to the trainee. Moreover, by providing the trainee with feedback and performance-based adaptation, the methods of the present disclosure can be more effective at improving self-regulation as compared to self-guided approaches. In addition, the effectiveness of the methods in improving the trainee's ability to regulate internal distraction unexpectedly enhances the trainee's performance on untrained cognitive tasks, as demonstrated in the Experimental section below.

The following example is offered by way of illustration and not by way of limitation.

Experimental

EXAMPLE 1

Enhancement of Cognitive Task Performance by Presentation of Focused Attention Tasks Experimental Design Interference is typically considered from an external perspective, but can also manifest as internal distraction (e.g., 'mind wandering') that interferes with the task at hand. In this example, subjects were presented with a mobile computer-based meditation-inspired training program (MT) that relies upon focused-attention meditation practices such as directing attention to breath sensations and the awareness of mind wandering. After each trial, the subjects were asked to indicate whether their attention remained entirely focused on their breathing for the duration of the trial. Their trial length was adjusted accordingly, using an adaptive staircase algorithm to push the limits of their ability to focus without being distracted.

Methods

The MT program was designed as an integration of meditation-based practices and approaches from plasticity-based, cognitive-training methods, including quantifiable goals, feedback and adaptivity. Participants began by starting a mobile application in a quiet location, free of external auditory distractions, with headphones on and eyes closed, and asked to attend to the sensations of their breath. Participants were asked to monitor the quality of their attention and to be particularly aware of any internal distracting thoughts that may arise. When these thoughts do occur, participants were asked to acknowledge the distraction, disengage from it, and shift their attention back to their breath. The length of the initial trial was set individually based on their thresholding result. At the end of each trial, participants reported via button-press whether their attention remained on their breath throughout the trial, or if their attention was diverted by distracting thoughts (e.g., mind-wandering). If they successfully attended to their breath on a trial, the duration of the next trial was increased by 20% of the length of the preceding trial; if unsuccessful, the duration of the next trial was decreased by 30% of the preceding trial length. By adaptively modifying the duration of the trials based on this criterion, the ability to self-regulate internal attention is selectively targeted. In addition, participants were provided regular feedback on their distractibility level throughout each session and at the end and beginning of each session (reflected as the trial duration, or the 'level' they achieved).

Results

Figure 4C:
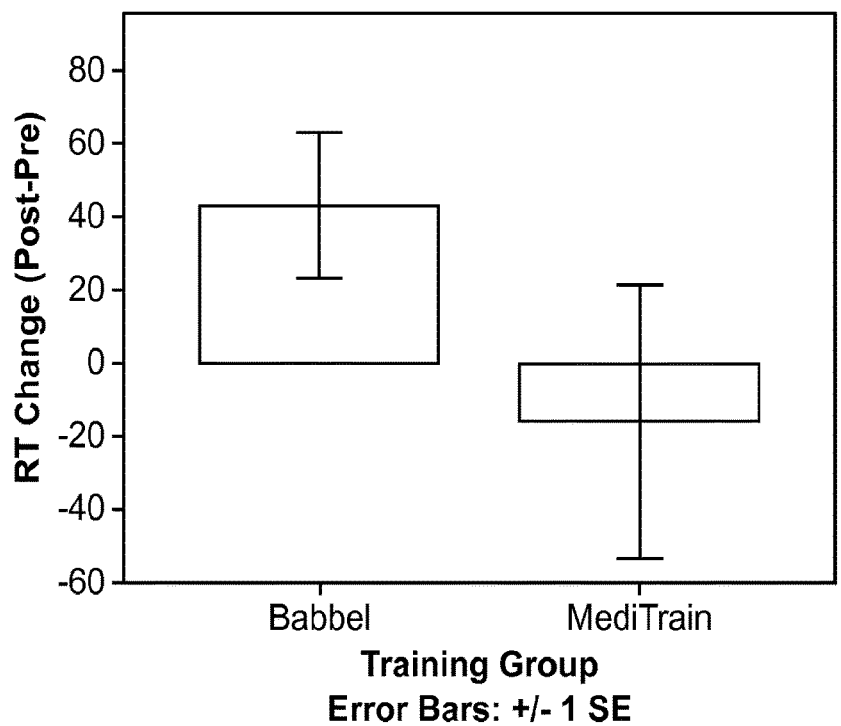
FIG. 4 provides data showing training-related improvements in the duration for which subjects could maintain focused attention over the course of a cognitive training program according to one embodiment of the present disclosure (Panels A and B). Also shown is data demonstrating the enhancement of performance on an untrained cognitive task as a result of the focused attention cognitive training program according to an embodiment of the present disclosure (Panels C and D).
Figure 4D:
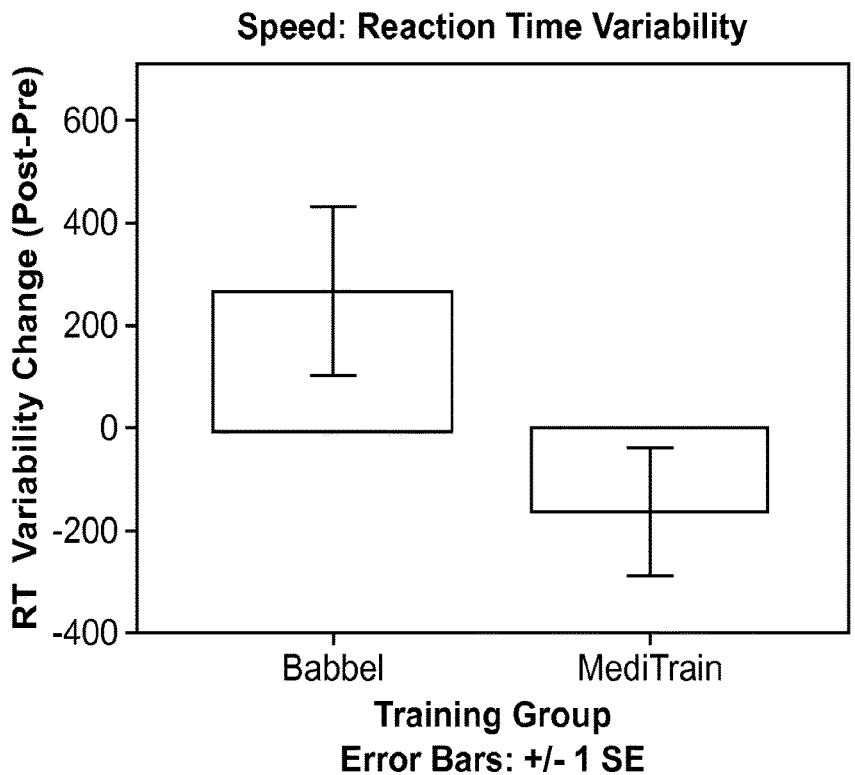

Younger adults (YA) (n=20, ages 21-28) and older adults (OA) (n=10, ages 57-75) completed either MT or a placebo control language-learning app for 20 minutes per day for 15 days. Results are shown in FIG. 4. MT participants showed training-related improvements in the time they could maintain focus on their breath (Panel A) and demonstrated a significant decrease in reports of internal distractions during an untrained working memory task. Both YA and OA showed a correlation between the reduction of internal distractions following training and the rate of improvement on the MT training (Panel B; for each group, $p \leq 0.001$; $r \geq -0.787$).

In addition, the training slope was highly correlated with post-training accuracy improvement on an untrained cognitive task, here an attentionally-demanding discrimination task ($p=0.007$; $R=0.914$). When collapsed across age groups, participants who completed MT demonstrated significant post-training improvements on i) a visual search task (Panel C; $p=0.021$) and ii) individual response time variability (Panel D; $p=0.045$), relative to the placebo training group that did not show an improvement.

These findings indicate that the training program not only improved the ability of subjects to suppress internal distractions/increase attention, but also leads to improvements in untrained, cognitive tasks/control abilities. These data indicate that regulation of internal distractions can be modified through practice with an application that integrates meditation principles with plasticity-based, cognitive training methods.

EXAMPLE 2

Training Program for Enhancing Cognitive Task Performance by Improved Self-Regulation of Internal Distraction Experimental Design It is unknown whether susceptibility to internal and external distractions relies on overlapping cognitive processes or if self-regulation of internal distractibility is amenable to cognitive training. This example involves a mobile meditation-inspired training program (referred to in this example as "MediTrain") that draws upon focused-attention meditation practices such as directing attention to breath sensations and the awareness of distractions. After each trial, participants are asked to indicate whether their attention remained entirely focused on their breath or if their mind wandered. The length of the next trial is adjusted accordingly, using an adaptive staircase algorithm to push the limits of their ability to focus without distraction.

Methods

This example involves a tablet computer-based, meditation-inspired cognitive training game aimed at improving self-regulation of internal distraction. This game is designed to make the benefits of meditation easily accessible to anyone, including complete novices. This was achieved by creating a game experience that yields quantifiable and attainable goals, provides both punctuated and continuous feedback, and includes an adaptive algorithm to increase difficultly as users improve. This novel "East meets West" approach focusing on core aspects of meditation (i.e., focused internal attention and awareness of distractions), reduces uncertainties that surround the benefits of traditional meditation, and allows the quantification of individual and group differences.

Figure 5:
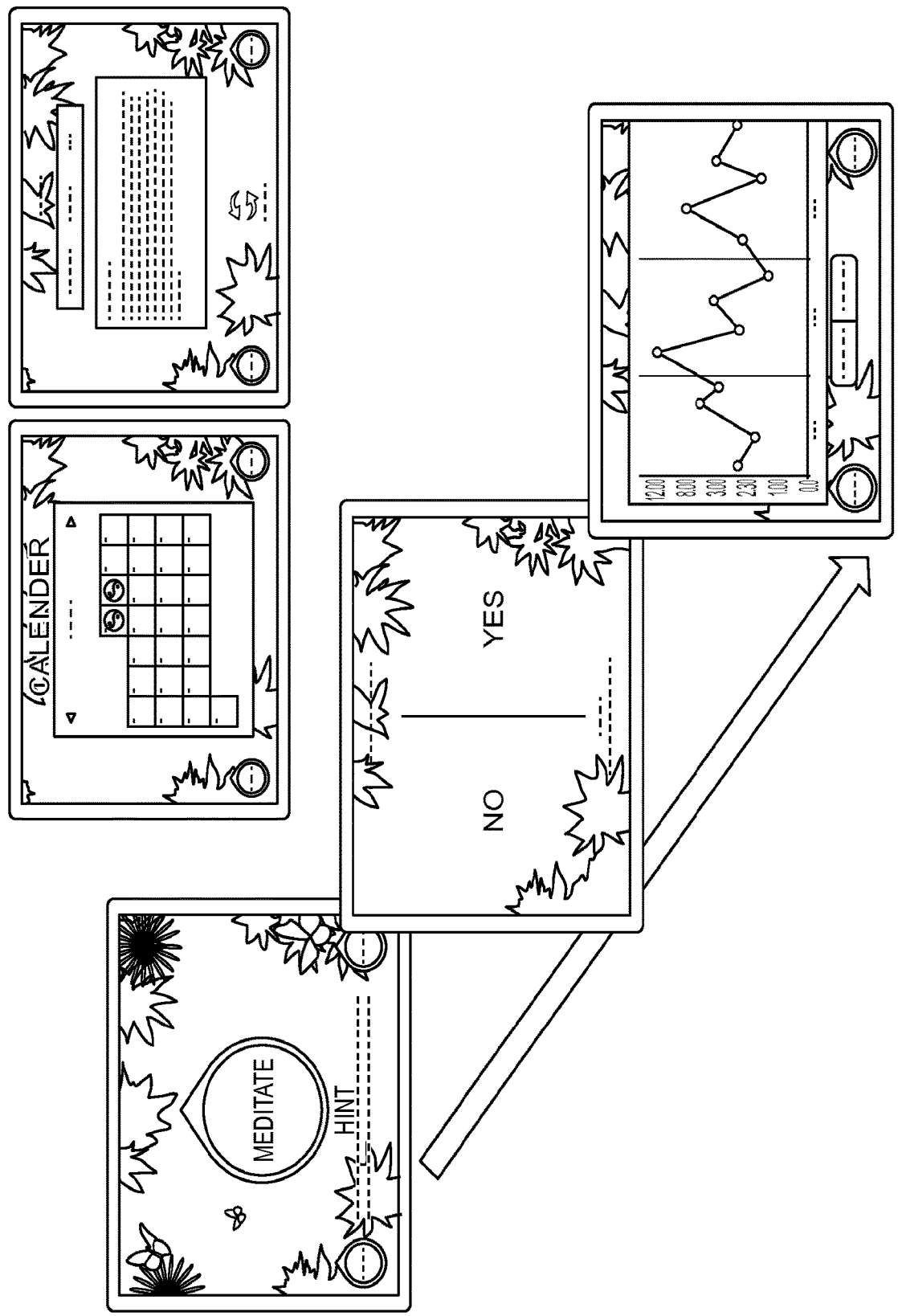
FIG. 5 shows screenshots of an example application showing progression through a meditation session followed by graphical feedback (left and bottom) as well as the progress calendar and "library" of meditation resources (top right).

Participants train with the application ("app") for 5 days per week for 6 weeks. Certain screenshots of this example application are shown in FIG. 5. The initial training time was 20 minutes per day and increased stepwise to 30 minutes in the final two weeks. It was hypothesized that this training would facilitate increased attention, supporting the ability to self-regulate internal distractions and avoid external distractions. In this example, participants begin by starting the mobile app in a quiet location, free of external auditory distractions, with headphones on and eyes closed, and attend to the sensations of their breath. Participants are asked to monitor the quality of their attention and to be particularly aware of any internal distracting thoughts that may arise. When these thoughts do occur, participants are asked to acknowledge the distraction, disengage from it, and shift their attention back to their breath. The length of the initial trial is set individually based on their thresholding result. At the end of each trial, participants report via button-press whether their attention remained on their breath throughout the trial, or if their attention was diverted by distracting thoughts (i.e., mind-wandering). If they successfully attended to their breath on a trial, the duration of the next trial is increased by 10% of the length of the preceding trial; if unsuccessful, the duration of the next trial is decreased by 20% of the preceding trial length. By adaptively modifying the duration of the trials based on this criterion, the ability to self-regulate internal attention is selectively targeted. In addition, participants are given regular feedback on their distractibility level throughout each session and at the end and beginning of each session (reflected as the trial duration, or the 'level' they achieved).

Results

Training data from healthy young adults who completed six weeks of training according to this example (MediTrain app) (n=11) or a placebo control app (n=12) was analyzed. MediTrain participants showed improvements in the time they could maintain focus on their breath over the six weeks of training. Further, the MediTrain group showed significant or trending improvements on two cognitive control tasks.

Figure 6:
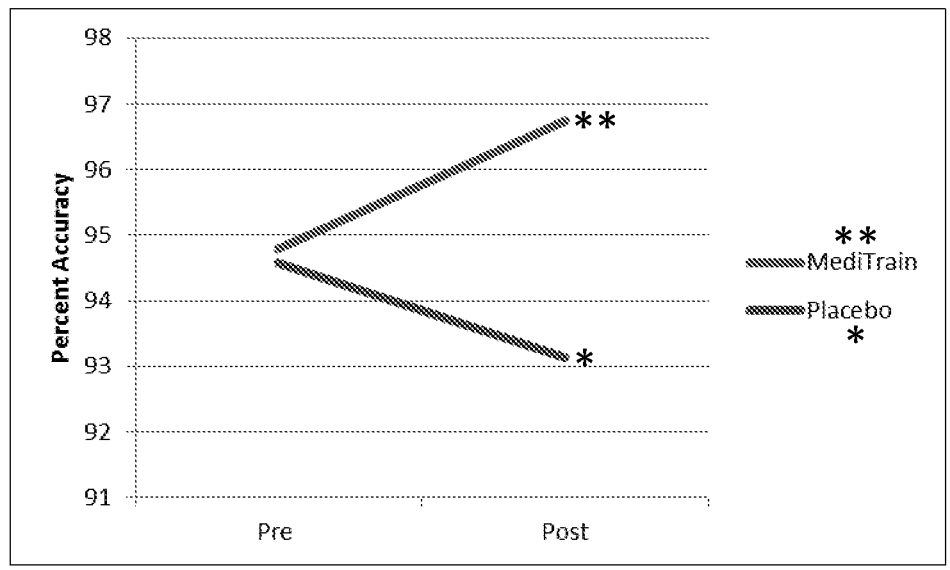
FIG. 6 provides data showing the accuracy for an example training program (MediTrain) (**) and placebo (*) before (pre) and after (post) training on a Filter Task with a set size of 1 memory item with distractors present.

The first cognitive control task is the Filter Task, in which participants must attend to an array of different numbers of items with visual distractors either present or absent. When compared to placebo, the Meditrain group showed a trend toward increased accuracy from Pre- to Post-training in the condition in which distractions are present (FIG. 6; Pre-Post independent t-test for Meditrain: p=0.006; Pre-Post independent t-test for placebo: ns; trending Session×Group Interaction: p=0.065).

Figure 7:
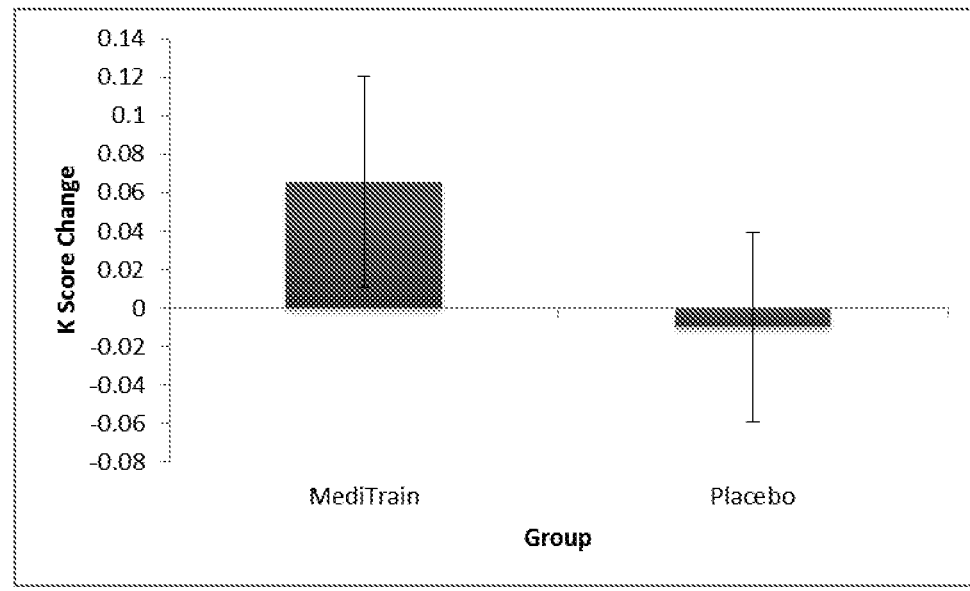
FIG. 7 provides data showing the change in working memory capacity (i.e., K scores) for an example training program (left) and placebo (right) groups from pre- to post-training.

The second cognitive control task is the Change Localization Task, which is a test of working memory capacity. Participants see an array of four colored dots and must indicate whether any of the colors change after a short delay. A "K score" is calculated for each participant, providing an index of their overall working memory capacity before and after training. After six weeks of training, the MediTrain group showed a trend toward a significant increase in K, while the placebo group remained unchanged (FIG. 7; p=0.1).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of enhancing the performance of a subject on an untrained cognitive task, comprising:
presenting a computer-based cognitive training program to a subject, wherein presenting the cognitive training program comprises:
(i) presenting to a subject, using a computer device comprising an input device, a first internally-directed focused attention task at a difficulty level;
(ii) determining, using the computer device, a duration that the subject maintained focused attention during presentation of the first internally-directed focused attention task, wherein determining the duration comprises receiving a response from the subject via the input device indicating the duration for which the subject maintained focused attention during presentation of the first internally-directed focused attention task; and
(iii) presenting to the subject, using the computer device, a second internally-directed focused attention task at an adapted difficulty level, wherein the adapted difficulty level is based on the duration for which the subject maintained focused attention during presentation of the first internally-directed focused attention task and is determined using an adaptive training algorithm, wherein the adaptive training algorithm comprises a staircase algorithm and/or maximum likelihood procedure wherein the internally-directed focused attention tasks are selected from the group consisting of: the subject directing attention to the subject's breath sensations, the subject directing attention to a mental image, the subject directing attention to a phrase held in the subject's mind, and the subject directing attention to a phrase held in an internal body part of the subject other than the mind, wherein the computer-based cognitive training program comprises performing steps (i) -(iii) each day over a number of days until the performance of the subject on the untrained cognitive task is enhanced by the cognitive training program.

2. The method according to claim 1, wherein the first internally-directed focused attention task and the second internally-directed focused attention task are the same.

3. The method according to claim 1, wherein the first internally-directed focused attention task and the second internally-directed focused attention task are different.

4. The method according to claim 1, wherein the difficulty level of the first focused attention task, the second focused attention task, or both, is determined by the duration of presentation thereof.

5. The method according to claim 1, wherein the difficulty level of the first focused attention task, the second focused attention task, or both, is determined by a context of presentation thereof.

6. The method according to claim 5, wherein the context comprises presenting one or more stimuli to the subject.

7. The method according to claim 6, wherein the one or more stimuli comprises an auditory stimulus.

8. The method according to claim 1, wherein the cutoff duration is the entire duration of presenting the first focused attention task.

9. The method according to claim 1, wherein the input device is selected from the group consisting of: a touchscreen display, a mouse, a keyboard, and a microphone.

10. The method according to claim 1, wherein determining the duration that the subject maintained focused attention during presentation of the first focused attention task comprises measuring one or more biological parameters of the subject.

11. The method according to claim 10, wherein the one or more biological parameters comprises neurological activity of the subject.

12. The method according to claim 11, wherein the neurological activity is measured by electroencephalography (EEG).

13. The method according to claim 12, wherein the neurological activity is measured by an EEG headset worn by the subject.

14. The method according to claim 10, wherein the one or more biological parameters comprises eye movement of the subject.

15. The method according to claim 1, wherein prior to presenting the first internally-directed focused attention task, the second internally-directed focused attention task, or both, the method comprises instructing the subject to notice internal distraction during presentation of the first internally-directed focused attention task, the second internally-directed focused attention task, or both.

16. The method according to claim 1, wherein the computer device is selected from the group consisting of: a smartphone, a tablet computer, a head-up display (HUD) device, a smartwatch, a laptop computer, a desktop computer, and combinations thereof.

17. The method according to claim 1, wherein the cognitive task is a visual search task.

18. The method according to claim 1, wherein the subject is an older adult.

19. A non-transitory computer-readable medium comprising instructions stored thereon for causing a computer device comprising an input device to present a cognitive training program to a subject to enhance the performance of the subject on an untrained cognitive task, wherein presenting the cognitive training program comprises:
   (i) presenting to a subject a first internally-directed focused attention task at a difficulty level;
   (ii) determining a duration that the subject maintained focused attention during presentation of the first internally-directed focused attention task, wherein determining the duration comprises receiving a response from the subject via the input device indicating the duration for which the subject maintained focused attention during presentation of the first internally-directed focused attention task; and
   (iii) presenting to the subject, using the computer device, a second internally-directed focused attention task at an adapted difficulty level, wherein the adapted difficulty level is based on the duration for which the subject maintained focused attention during presentation of the first internally-directed focused attention task and is determined using an adaptive training algorithm, wherein the adaptive training algorithm comprises a staircase algorithm and/or maximum likelihood procedure, wherein the internally-directed focused attention tasks are selected from the group consisting of: the subject directing attention to the subject's breath sensations, the subject directing attention to a mental image, the subject directing attention to a phrase held in the subject's mind, and the subject directing attention to a phrase held in an internal body part of the subject other than the mind, and wherein the computer-based cognitive training program comprises performing steps (i) -(iii) each day over a number of days until the performance of the subject on the untrained cognitive task is enhanced by the cognitive training program.

20. A computer device comprising an input device and a non-transitory computer-readable medium comprising instructions stored thereon for causing the computer device to present a cognitive training program to a subject to enhance the performance of the subject on an untrained cognitive task, wherein presenting the cognitive training program comprises:
   (i) presenting to a subject a first internally-directed focused attention task at a difficulty level;
   (ii) determining a duration that the subject maintained focused attention during presentation of the first internally-directed focused attention task, wherein determining the duration comprises receiving a response from the subject via the input device indicating the duration for which the subject maintained focused attention during presentation of the first internally-directed focused attention task; and
   (iii) presenting to the subject, using the computer device, a second internally-directed focused attention task at an adapted difficulty level, wherein the adapted difficulty level is based on the duration for which the subject maintained focused attention during presentation of the first internally-directed focused attention task and is determined using an adaptive training algorithm, wherein the adaptive training algorithm comprises a staircase algorithm and/or maximum likelihood procedure, wherein the internally-directed focused attention tasks are selected from the group consisting of: the subject directing attention to the subject's breath sensations, the subject directing attention to a mental image, the subject directing attention to a phrase held in the subject's mind, and the subject directing attention to a phrase held in an internal body part of the subject other than the mind, and wherein the computer-based cognitive training program comprises performing steps (i) -(iii) each day over a number of days until the performance of the subject on the untrained cognitive task is enhanced by the cognitive training program.

* * * * *